United States Patent

Mehra et al.

[11] Patent Number: 6,013,282
[45] Date of Patent: Jan. 11, 2000

[54] ENTERIC FILM COATING COMPOSITIONS, METHOD OF COATING THEREWITH, AND COATED FORMS

[75] Inventors: Dev K. Mehra, Furlong; Chittamuru Ramireddy, Lansdale; Li-Juan Tang, Norristown; Stuart C. Porter, Hatfield, all of Pa.

[73] Assignee: Bpsi Holdings, Inc., Wilmington, Del.

[21] Appl. No.: 08/978,661

[22] Filed: Nov. 26, 1997

Related U.S. Application Data

[62] Division of application No. 08/319,987, Oct. 7, 1994, Pat. No. 5,733,575.

[51] Int. Cl.[7] .................................................. A61K 9/36
[52] U.S. Cl. ........................ 424/480; 424/489; 424/464; 424/490
[58] Field of Search ................................... 424/480, 489, 424/490, 457, 35

[56] References Cited

U.S. PATENT DOCUMENTS 4,001,390  1/1977  Ohno et al. .
5,356,467  10/1994  Oshlack et al. .
5,622,721  4/1997  Dansereau et al. .

*Primary Examiner*—Thurman K. Page
*Assistant Examiner*—William E. Benston, Jr.
*Attorney, Agent, or Firm*—John F. A. Earley; John F. A. Earley III; Harding, Earley, Follmer & Fraiely

[57] ABSTRACT

A non-toxic edible enteric film coating dry powder composition for use in making an aqueous enteric coating suspension which may be used in coating pharmaceutical tablets and the like comprises an enteric film forming polymer, a detackifier, a viscosity modifier, and an alkalizing/anti-coagulating agent. Advantageously, the inventive dry powder compositions may include a solid plasticizer, a lubricant, an anti-caking agent, a liquid plasticizer, and a pigment.

5 Claims, 1 Drawing Sheet

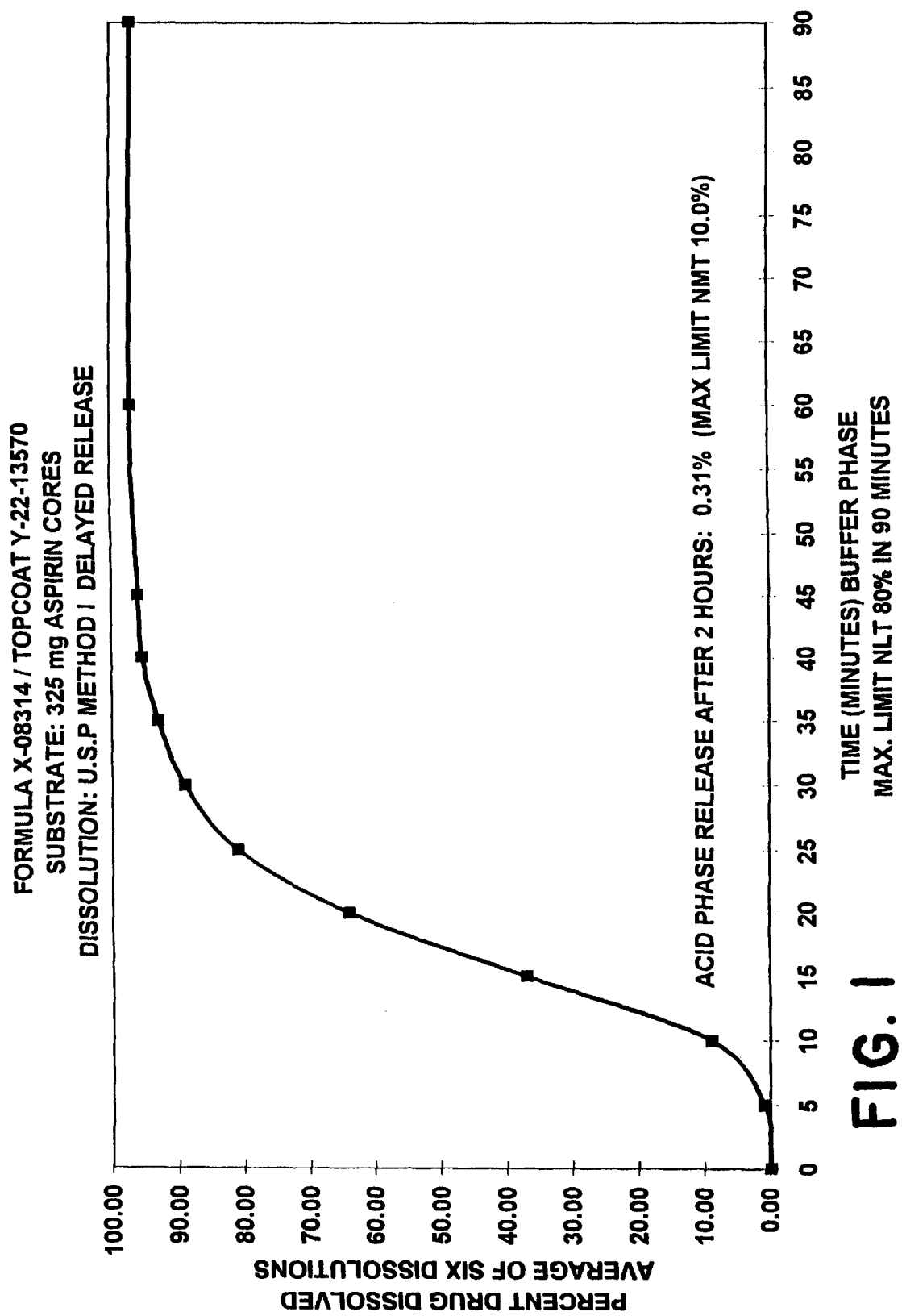

ENTERIC FILM COATING COMPOSITIONS, METHOD OF COATING THEREWITH, AND COATED FORMS

This is a divisional of application Ser. No. 08/319,987 filed on Oct. 7, 1994 now U.S. Pat. No. 5,733,575.

FIELD OF THE INVENTION

This invention relates to the field of aqueous enteric film coating suspensions for coating pharmaceutical tablets and the like for preventing release of the ingredients of the coated tablet in the gastric juices of the stomach, and for releasing the ingredients of the tablet in the intestines. It provides a non-toxic edible enteric film coating dry powder composition for use in making an aqueous enteric coating suspension that may be used in coating pharmaceuticals with an intestinally soluble coating that is insoluble in the gastric juices of the stomach.

BACKGROUND OF THE INVENTION

Enteric coating solutions that require organic solvents have been used in the past. However, because of the problems associated with the use of organic solvents (ie., pollution of the atmosphere, safety and hygiene problems for workers, danger of fire and explosion, and expensive equipment requirements to limit or reduce the danger of fire or explosion), aqueous enteric film coating suspensions, such as the COATERIC enteric film coating system of Colorcon, West Point, Pa., were developed. The COATERIC system is disclosed in Colorcon U.S. Pat. No. 4,556,552, which issued on Dec. 3, 1985, and in Colorcon U.S. Pat. No. 4,704,295 which issued on Nov. 3, 1987, both of which are incorporated herein by reference.

Other known aqueous enteric film coating systems include an aqueous dispersion of acrylic resins, for example, polymethacryl methacrylate copolymer, and dispersions of acetates, for example, cellulose acetate phthalate.

A problem associated with the known aqueous enteric coating suspensions is tackiness of the coating.

Another problem with the known aqueous enteric coating systems is that they require at least three processing steps to form the enteric coating suspension. For instance, with the EUDRAGIT system, plasticizer, antifoam, and talc are mixed stepwise into the EUDRAGIT dispersion. With the AQUATERIC—celllulose acetate phthalate dispersion system, the AQUATERIC powder is dispersed in water, followed by stepwise addition of plasticizer, and Tween 80 to form the AQUATERIC suspension. With the COATERIC system, the COATERIC powder, an antifoam, and ammonium hydroxide are mixed into water to form the COATERIC suspension. The need for three processing steps is a drawback because the more processing steps there are, the higher the chances of processing error occurring.

In the Colorcon U.S. Pat. Nos. 4,556,552 and 4,704,295, Colorcon's COATERIC non-toxic edible enteric film coating dry powder, which comprises polyvinyl acetate phthalate (PVAP), a water-soluble plasticizer, an auxiliary film-forming suspending polymeric agent for the PVAP, and pigment particles, is mixed into water, and after the enteric dry powder is thoroughly wetted, an ammonium hydroxide solution is added to form an enteric coating suspension. Although the COATERIC coating suspension forms a very good enteric coating, the COATERIC suspension has the smell of ammonium hydroxide.

SUMMARY OF THE INVENTION

It is an object of the invention to provide an enteric coating that is less tacky than known aqueous-based enteric film coatings.

Another object of the invention to provide an aqueous enteric coating suspension that only requires two processing steps to form the enteric coating suspension.

Another object of the invention is to provide an aqueous enteric coating suspension that does not have the odor of ammonium hydroxide.

Another object of the invention is to provide a pre-plasticized powder blend enteric coating composition.

These and other objects are accomplished by our invention, which is described below.

BRIEF DESCRIPTION OF THE DRAWINGS

FIG. 1 shows a graph of test results regarding percent drug dissolved (average of 6 dissolutions) versus time (minutes), for aspirin cores coated in accordance with Example 1.

DETAILED DESCRIPTION OF THE INVENTION

A non-toxic edible enteric film coating dry powder composition for use in making an aqueous enteric coating suspension which may be used in coating pharmaceutical tablets and the like comprises an enteric film forming polymer, a detackifier, a viscosity modifier, and an alkalizing/anti-coagulating agent. In a particularly preferred embodiment, the inventive non-toxic edible enteric film coating dry powder composition also includes a solid plasticizer.

Advantageously, the inventive dry powder compositions may include a lubricant, an anti-caking agent, a liquid plasticizer, and a pigment.

A method of making the inventive non-toxic edible film coating dry powder composition comprises the steps of mixing an enteric film forming polymer with a detackifier, a viscosity modifier, and an anti-coagulating/alkalizing agent, and optionally with one or more of the following components, until a dry homogeneous powder mixture is produced: a solid plasticizer, a lubricant, an anti-caking agent, a liquid plasticizer, and a pigment. The resulting enteric film coating dry powder composition is readily dispersible in deionized water to form a liquid enteric coating suspension and is ready to use in 30 to 45 minutes.

The invention also includes an aqueous enteric coating suspension for making an enteric coating for pharmaceutical tablets and the like which comprises an enteric film forming polymer, a detackifier, a viscosity modifier, an alkalizing agent, a plasticizer, and an antifoaming agent mixed into water. Advantageously, the inventive suspension may include an optional lubricant, an optional anti-caking agent, and/or an optional pigment.

A method of making the aqueous enteric coating suspension of the invention comprises mixing the anti-foaming agent into water, mixing the inventive enteric dry powder composition, or the individual ingredients of the inventive enteric dry powder composition separately, into the water, and stirring until a homogeneous suspension is produced. When using an embodiment of the inventive enteric dry powder composition that does not have a plasticizer mixed into it, a plasticizer, preferably a liquid plasticizer, is mixed into the water, preferably after the step of mixing the anti-foam into the water.

The inventive suspension may include a solid plasticizer in combination with a liquid plasticizer. In such a suspension, the liquid plasticizer may be mixed into the enteric dry powder coating composition to become part of the enteric dry powder coating composition of the invention, or the liquid plasticizer may be added separately to the water when preparing the inventive suspension.

The invention also includes a method of coating substrates such as pharmaceutical dosage forms like tablets and the like with a non-toxic edible enteric film coating, which comprises the steps of forming the inventive aqueous enteric coating suspension as discussed above, applying the inventive aqueous coating suspension onto the substrates to form a film coating on the substrates, and drying the film coating on said substrates.

The enteric film forming polymer is PVAP-T (titanized polyvinyl acetate phthalate), PVAP-J (polyvinyl acetate phthalate which has been jet milled), HPMCP (hydroxypropyl methylcellulose phthalate), HPMCAS (hydroxypropyl methylcellulose acetate succinate), or CAP (cellulose acetate phthalate). The titanized polyvinyl acetate phthalate (PVAP-T), comprises about 10% titanium dioxide mixed into polyvinyl acetate phthalate (PVAP), while it is being made. A preferred enteric polymer is PVAP-T.

Preferably, the enteric polymer has a particle size such that 90% of the polymer particles are under 25 microns, and more preferably, under 13 microns.

The enteric polymer is about 65–85% by weight of the dry powder composition, and is preferably in the range of about 65–81% by weight of the dry powder composition.

The detackifier is talc, aluminum hydrate, or mixtures thereof. The detackifier is about 5–15% by weight of the dry powder composition, and is preferably in the range of about 6–12% by weight of the dry powder composition.

The viscosity modifier is sodium alginate, hydroxypropyl methylcellulose (HPMC), hydroxyethylcellulose (HEC), sodium carboxymethycellulose (sodium CMC), polyvinylpyrrolidone (PVP), Konjac flour, carrageenan, xanthan gum, other hydrophilic polymers, or mixtures thereof. The viscosity modifier is present in the dry powder composition to assist in the forming of a film on the tablets and to act as a suspending agent for the insoluble components in the coating suspension, as well as adding viscosity to the coating suspension. The viscosity modifier helps the coating to adhere to the tablet surface while the enteric polymer particles are fusing to form a film. In other words, the viscosity modifier makes the coating suspension thicker and thereby inhibits settlement and acts as a suspending agent, and also acts as a film former. A preferred viscosity modifier is a medium viscosity grade of sodium alginate (e.g., Kelco Manugel A3B812 sodium alginate).

The viscosity modifier is about 0.5 to 7% by weight of the dry powder composition, and is preferably in the range of about 1–6% by weight of the dry powder composition.

The alkalizing agent is a bicarbonate, a carbonate, a phosphate, or a hydroxide of sodium or potassium, magnesium carbonate, magnesium hydroxide, ammonium carbonate, ammonium bicarbonate, magnesium oxide, calcium hydroxide, or mixtures thereof.

The alkalizing agent is about 1–15% by weight of the dry powder composition, and is preferably in the range of about 1.5–12% by weight of the dry powder composition. Sodium bicarbonate and/or sodium carbonate as the alkalizing agent are preferably used in a range of about 2.0% to about 6% by weight of the dry power composition, and more preferably used in a range of about 2.0% to about 4.5% since above 6% may lead to tackiness problems. When using tri-sodium phosphate as the alkalizing agent, a range of 4.5% to 7% by weight of the dry power composition is preferred for tri-sodium phosphate (anhydrous) and a range of 8% to 12% by weight of A the dry power composition is preferred for tri-sodium phosphate (hydrated).

The alkalizing agent acts as an anti-coalescing or stabilizing agent to raise the agglomeration or gel temperature of the coating suspension to prevent coalescing or blockage of the spray lines and guns. The alkalizing agent also reduces the tackiness of the coating.

The solid plasticizer is polyethylene glycol having a molecular weight of 1500 to 8000, or Pluronic F86 (a block co-polymer of ethylene oxide and propylene oxide (EO/PO)), or mixtures thereof. The preferred solid plasticizer is polyethylene glycol 3350 (PEG 3350) or polyethylene glycol 4000 (PEG 4000).

The solid plasticizer when included in the inventive enteric dry powder composition is about 1–20% by weight of the dry coating composition, and is preferably about 1–18% by weight of the dry coating composition.

The liquid plasticizer may be triethylcitrate, glyceryl triacetate, acetyltriethylcitrate, dibutyl sebacate, diethyl phthalate, polyethylene glycol 400, glycerol, castor oil, or mixtures thereof.

When the liquid plasticizer is included in the dry powder composition of the invention, the liquid plasticizer is in a range of greater than 0% to about 6% by weight of the dry powder composition. The dry powder composition of the invention is still dry even though it may contain about 4–6% liquid plasticizer by weight of the dry powder composition.

When no plasticizer is included in the dry powder coating composition of the invention or when no liquid plasticizer is included in the dry powder coating composition of the invention, about 5% to about 20% of liquid plasticizer by weight of the dry solid ingredients of the coating suspension of the invention is mixed separately into the coating suspension of the invention.

The inventive coating suspension has about 5% to about 20% of solid plasticizer, liquid plasticizer, or a combination of solid plasticizer and liquid plasticizer by weight of the non-water ingredients of the inventive coating suspension.

The lubricant is stearic acid, which is in a range from 0% to about 3% by weight of the dry coating composition.

The anti-caking agent may be Cabosil, fumed silica made by Cabot, Inc., which is present in a range from 0% to about 2% by weight of the dry powder composition, and preferably is present in a range from 0% to 1.5% by weight of the dry powder coating composition. The anti-caking agent acts as a processing aid and also keeps the dry powder from lumping up while in storage. Use of this anti-caking agent is optional because any lumps that are formed are screened out as part of the preparation of the dispersion.

The pigment may be any of the pigments used in making coating dispersions for pharmaceutical tablets and the like. For example, the pigments may be FD&C and D&C lakes, titanium dioxide, magnesium carbonate, talc, pyrogenic silica, iron oxides, channel black, and insoluble dyes. Also, natural pigments such as riboflavin, carmine 40, curcumin, and annatto. Other examples of suitable pigments are listed in Jeffries U.S. Pat. No. 3,149,040; Butler et al. U.S. Pat. No. 3,297,535; and Colorcon U.S. Pat. No. 3,981,984; all of which are incorporated herein by reference.

The pigment may also include lake blends, which contain a plasticizer, and OPADRY pigmented coating compositions, some of which are disclosed in Colorcon U.S. Pat. No. 4,543,370 issued on Sept. 24, 1985, which is incorporated herein by reference.

The pigment, in addition to adding color to the coating of the invention, also acts as an anti-gelling agent.

The pigment is in a range from 0% to about 25% by weight of the dry coating composition, and preferably is in a range from 0% to about 15% by weight of the dry powder composition.

The antifoaming agent is a silicone based antifoam, such as Antifoam FG-10 made by Dow Corning. The antifoaming agent is in a range from about 0.1% to about 5% by weight of the dry powder composition, and is preferably about 0.5% to about 5% by weight of the dry powder composition.

The inventive dry powder non-toxic enteric coating composition is to be made and sold by Colorcon, West Point, Pa. 19486, under the trademark SURETERIC.

The following examples further illustrate the invention.

EXAMPLE 1

12 kilograms of aspirin cores (325mg of aspirin per tablet) are to be coated with a clear subcoat made from a clear OPADRY coating dispersion, an enteric coating of the invention over the subcoat, and a pigmented topcoat over the enteric coating, the topcoat being made from an OPADRY II coating dispersion.

The clear OPADRY subcoat dispersion of this Example 1 is made by mixing 120 grams of clear OPADRY coating composition (formula YS-2-7013) into 1480.0 grams of deionized water using a propeller mixer for 45–60 minutes to obtain the subcoat suspension. The subcoat suspension has 7.5% w/w total solids. The OPADRY coating composition is manufactured by Colorcon, West Point, Pa.

The inventive SURETERIC enteric dry powder composition of this Example 1 is prepared by throughly mixing 24.00 grams of the liquid plasticizer, Citroflex triethylcitrate, into 876.00 grams of PVAP-T in a V-blender. Then, 113.52 grams of talc, 40.80 grams of sodium bicarbonate, 96.00 grams of PEG 3350, 21.60 grams of stearic acid, 16.80 grams of sodium alginate, and 11.28 grams of Cabosil EH5 silica is added to the mixture of PVAP-T and liquid plasticizer and mixed into it for about 10 minutes. The mixture then is passed through a grinder, and then mixed again for 10 more minutes.

The inventive enteric suspension of the invention is prepared by mixing 1200.0 grams of the inventive enteric dry powder composition into 6800.0 grams of deionized water in a blender for about 1 hour. Before adding the enteric dry powder composition to the water, 12 grams of a 10% Antifoam FG-10 solution is mixed into the 6800.0 grams of distilled water. The total solids in the enteric suspension is 15.0% w/w.

The pigmented OPADRY II topcoat suspension is prepared by mixing 360.0 grams of pigmented OPADRY II coating composition (formula Y-22-13570) into 1440.0 grams of distilled water using a propeller mixer for 45–60 minutes. The total solids in the topcoat suspension is 20% w/w. The pigmented OPADRY II coating composition is made by Colorcon, West Point, Pa.

The enteric suspension is passed through a 60 mesh screen prior to commencement of spraying.

The 12 kilograms of aspirin cores (352 mg of aspirin per tablet) are placed in a 24 inch Accela-Cota pan, which has 4 mixing baffles, a Cole-Parmer Masterflex pump having 2 pump heads, Silicone 7015 tubing, 2 Binks 605 spray guns, 66SS fluid nozzles, and 66SH air caps, for coating. The tablets are first given a subcoat using a clear OPADRY subcoat suspension, followed by an enteric coating with the enteric suspension of this Example 1, which is followed by a topcoat of the pigmented OPADRY II topcoat suspension. The spraying conditions are as follows:

|  | SUBCOAT | ENTERIC COAT | TOP COAT |
|---|---|---|---|
| TABLET LOAD (kg) | 12 | 12 | 12 |
| FLUID RATE (g/min) | 60 | 70 | 60 |
| ATOMIZING AIR (psi) | 35 | 35 | 35 |
| AIR TEMPERATURE (° C.) |  |  |  |
| INLET | 70 | 69 | 67 |
| EXHAUST | 43 | 41 | 43 |
| PAN SPEED (rpm) | 15 | 15 | 15 |
| COATING TIME (min) | 27 | 114 | 30 |
| POST DRYING | none | none | none |
| % WEIGHT GAIN | 1 | 10 | 3 |

The final coated tablets were evaluated using a modified U.S.P. disintegration method. 50 tablets were stressed for 100 revolutions in a fibrilator. Then, the 50 stressed tablets were placed in a basket assembly and immersed for 1 hour in simulated gastric fluid. The basket was moved up and down in the simulated gastric fluid at a rate of about 28–32 strokes/min. 50 unstressed tablets were also placed in a basket assembly and immersed for 1 hour in simulated gastric fluid. The basket was moved up and down in the simulated gastric fluid at a rate of about 28–32 strokes/min.

The integrity of the tablets was evaluated after removal from the simulated gastric fluid. None of the tablets exhibited signs of bloating, cracks, or fissures.

The results of the tests are as follows:
UNSTRESSED: 0% FAILURE
STRESSED: 0% FAILURE A dissolution test was also made on the coated tablets of this Example 1. Using U.S.P. apparatus I (baskets), 6 tablets coated as described in this Example 1 were placed in 0.1N HCL for 2 hours. The release in the acid phase of the test after 2 hours was 0.31%, as compared with the upper limit of not more than 10%. The 6 tablets were then placed in 6.8 phosphate buffer, and the amount of aspirin released in the buffer phase of the test was greater than 85% in thirty minutes, as compared with the official compendial requirement of not less than 80% in 90 minutes. These test results are illustrated in the graph shown in FIG. 1.

EXAMPLE 2

12 kilograms of Diclofenac sodium cores (75mg Diclofenac sodium per tablet) are to be coated with a clear subcoat made from a clear OPADRY coating dispersion, an enteric coating of the invention over the subcoat, and a clear topcoat over the enteric coating, the topcoat also being made from an OPADRY coating dispersion. Diclofenac sodium cores are alkaline substrates, and it is very difficult to coat alkaline substrates with an enteric coating.

The clear OPADRY subcoat dispersion and the clear OPADRY topcoat dispersion of this Example 2 are each made by mixing 120 grams of clear OPADRY coating composition (formula YS-2-7013) into 1480.0 grams of deionized water using a propeller mixer for 45–60 minutes to obtain the subcoat and topcoat suspensions. The subcoat suspension and the topcoat suspension each have 7.5% w/w total solids. The OPADRY coating composition is manufactured by Colorcon, West Point, Pa.

The inventive SURETERIC enteric dry powder composition of this Example 2 is prepared by throughly mixing 24.00 grams of the liquid plasticizer, Citroflex triethylcitrate, into 876.00 grams of PVAP-T in a V-blender. Then, 113.52 grams of talc, 40.80 grams of sodium bicarbonate, 96.00 grams of PEG 3350, 21.60 grams of stearic acid, 16.80 grams of sodium alginate, and 11.28 grams of Cabosil EH5 silica are added to the mixture of PVAP-T and liquid plasticizer and mixed into the mixture for about 10 minutes. The mixture then is passed through a grinder, and then mixed again for 10 more minutes.

The inventive enteric suspension of the invention is prepared by mixing 1200.0 grams of the inventive enteric dry powder composition into 6800.0 grams of deionized water in a blender for about 1 hour. Before adding the enteric dry powder composition to the water, 12 grams of a 10% Antifoam FG-10 solution is mixed into the 6800.0 grams of distilled water. The total solids in the enteric suspension is 15.0% w/w.

The enteric suspension is passed through a 60 mesh screen prior to commencement of spraying.

The 12 kilograms of Diclofenac sodium cores (75 mg Diclofenac sodium per tablet) are placed in a 24 inch Accela-Cota pan, which has 4 mixing baffles, a Cole-Parmer Masterflex pump having 2 pump heads, Silicone 7015 tubing, 2 Binks 605 spray guns, 66SS fluid nozzles, and 66SH air caps, for coating. The tablets are first given a subcoat using the clear OPADRY subcoat suspension, followed by an enteric coating with an enteric suspension of this Example 2, which is followed by a topcoat of the OPADRY suspension. The spraying conditions are as follows:

|  | SUBCOAT | ENTERIC COAT | TOP COAT |
|---|---|---|---|
| TABLET LOAD (kg) | 12 | 12 | 12 |
| FLUID RATE (g/min) | 60 | 70 | 60 |
| ATOMIZING AIR (psi) | 35 | 35 | 35 |
| AIR TEMPERATURE (° C.) | | | |
| INLET | 74 | 72 | 72 |
| EXHAUST | 43 | 41 | 43 |
| PAN SPEED (rpm) | 15 | 15 | 15 |
| COATING TIME (min) | 27 | 114 | 27 |
| POST DRYING | none | none | none |
| % WEIGHT GAIN | 1 | 10 | 3 |

The final coated tablets were evaluated using a modified U.S.P. disintegration method. 50 tablets were stressed for 100 revolutions in a fribilator. Then, the 50 stressed tablets were placed in a basket assembly and immersed for 1 hour in simulated gastric fluid. The basket was moved up and down in the simulated gastric fluid at a rate of about 28–32 strokes/min.

50 unstressed tablets were also placed in a basket assembly and immersed for 1 hour in simulated gastric fluid. The basket was moved up and down in the simulated gastric fluid at a rate of about 28–32 strokes/min.

The integrity of the tablets was evaluated after removal from the simulated gastric fluid. None of the tablets exhibited signs of bloating, cracks, or fissures.

The results of the tests are as follows:

UNSTRESSED: 0% FAILURE

STRESSED: 0% FAILURE

Six of the 50 stressed tablets from the simulated gastric fluid dissolution test and six of the 50 unstressed tablets from the simulated gastric dissolution test were placed in a basket assembly and immersed for one hour in simulated intestinal fluid. The basket was moved up and down in the simulated intestinal fluid at a rate of about 28–32 strokes per minute. The six stressed tablets and the six unstressed tablets all disintegrated within 8 minutes.

Examples 3–93 further illustrate the invention, all percentages being by weight. In examples 3, 5–9, 11–21, 24, 27, 28, 33–44, 52, 61, and 62, the components of each formulation are mixed together, formed into an enteric coating suspension, and applied to tablets, as in Examples 1 and 2.

In Examples 4, 10, 23, 29–32, 45–51, 53–60, and 80–93, the components of the formulations are dry mixed together to form the enteric dry powder composition, and then the enteric dry powder composition is formed into an enteric coating suspension and applied to tables as in Examples 1 and 2.

In Examples 22, 25, 26, and 63–79, the dry components are mixed together to form the enteric dry powder composition, which is added to water containing antifoam and the liquid plasticizer of the example.

| SURETERIC FORMULATIONS | | | | | | | |
|---|---|---|---|---|---|---|---|
| Raw Material | #3 | #4 | #5 | #6 | #7 | #8 | #9 |
| PVAP-T | 65.00 | 81.00 | 75.00 | 68.00 | 73.00 | 73.00 | 73.00 |
| Talc 400 | 12.00 | 7.00 | 6.00 | 12.00 | 8.50 | 9.00 | 9.50 |
| Stearic Acid | 2.60 | 0.00 | 2.60 | 2.60 | 1.60 | 1.60 | 1.80 |
| Sodium Alginate | 1.80 | 1.30 | 1.40 | 1.60 | 1.00 | 2.00 | 1.40 |
| PEG 3350 | 12.00 | 6.90 | 8.40 | 9.40 | 8.30 | 8.00 | 6.00 |
| Citroflex-2 | 2.40 | 0.00 | 2.20 | 2.20 | 2.00 | 2.00 | 4.00 |
| Sodium bicarbonate | 3.00 | 3.60 | 3.40 | 3.20 | 3.40 | 3.40 | 3.40 |
| Cabosil EH 5 | 1.20 | 0.30 | 1.00 | 1.00 | 1.00 | 1.00 | 0.90 |
| Total | 100.00 | 100.00 | 100.00 | 100.00 | 100.00 | 100.00 | 100.00 |
| Raw Material | #10 | #11 | #12 | #13 | #14 | #15 | #16 |
| PVAP-T | 67.0 | 75.00 | 73.00 | 75.00 | 74.00 | 73.00 | 73.00 |
| Talc 400 | 8.00 | 9.00 | 8.40 | 9.00 | 9.00 | 8.90 | 8.90 |
| Stearic Acid | 1.50 | 0.00 | 2.80 | 1.80 | 2.00 | 1.80 | 1.30 |
| Sodium Alginate | 1.40 | 1.50 | 1.40 | 1.40 | 1.50 | 1.40 | 1.40 |
| PEG 3350 | 18.00 | 8.00 | 8.00 | 7.80 | 8.00 | 8.00 | 8.00 |

-continued

SURETERIC FORMULATIONS

| | | | | | | | |
|---|---|---|---|---|---|---|---|
| Citroflex-2 | 0.00 | 2.00 | 2.00 | 2.20 | 2.00 | 2.00 | 2.00 |
| Sodium bicarbonate | 3.20 | 3.40 | 3.40 | | 3.40 | 3.40 | 3.40 |
| Sodium Hydroxide | | | | 2.00 | | | |
| Cabosil EH 5 | 0.90 | 1.10 | 1.00 | 1.00 | 0.00 | 1.50 | 2.00 |
| Total | 100.00 | 100.00 | 100.00 | 100.00 | 100.00 | 100.00 | 100.00 |

| Raw Material | #22 | #23 | #24 | #25 | #26 | #27 | #28 |
|---|---|---|---|---|---|---|---|
| PVAP-J | 78.50 | 65.00 | 65.00 | 71.00 | 81.00 | 68.00 | 73.00 |
| Talc 400 | 8.00 | 8.00 | 9.00 | 9.00 | 11.00 | 9.50 | 10.50 |
| Stearic Acid | | 1.50 | 1.80 | 1.80 | 1.80 | 1.30 | 1.70 |
| Sodium Alginate | 1.50 | 1.40 | 1.50 | 1.40 | 1.60 | | |
| HPMC E-50 | | | | | | 7.00 | |
| HEC (Natrosol 250 HR) | | | | | | | 0.50 |
| PEG 3350 | | 20.00 | 10.00 | 12.50 | | 8.00 | 8.00 |
| Citroflex-2 | *11.95 | 0.00 | 0.50 | *5.00 | *20.00 | 2.00 | 2.00 |
| Tri Sodium Phosphate | 12.00 | | | | | | |
| Sodium bicarbonate | | 3.20 | 3.20 | 3.40 | 3.60 | 3.40 | 3.40 |
| Cabosil EH 5 | | 0.90 | 1.00 | 0.90 | 0.90 | 1.00 | 0.90 |
| Total | 100.00 | 100.00 | 100.00 | 100.00 | 100.00 | 100.00 | 100.00 |

| Raw Material | #29 | #30 | #31 | #32 | #33 | #34 | #35 |
|---|---|---|---|---|---|---|---|
| PVAP-T | 68.00 | 69.00 | 69.00 | 73.50 | 74.10 | 73.00 | 73.00 |
| Talc 400 | — | — | 8.88 | 9.14 | 10.00 | 9.46 | 9.46 |
| Aluminium Hydrate | 10.30 | 8.65 | — | — | — | — | — |
| Stearic Acid | 2.80 | 1.90 | 1.76 | 1.72 | 1.80 | 1.80 | 1.80 |
| Sodium Alginate | 1.40 | 1.40 | 1.33 | 1.42 | 1.44 | 1.40 | 1.40 |
| PEG 3350 | 10.36 | 9.28 | 6.65 | 9.30 | 7.20 | — | — |
| Pluronic F68 | — | — | 3.00 | — | — | — | — |
| PEG 4000 | — | — | — | — | — | — | 8.00 |
| PEG 8000 | — | — | — | — | — | 8.00 | — |
| Citroflex-2 | — | — | — | — | 2.00 | 2.00 | 2.00 |
| Sodium Bicarbonate | — | — | — | — | — | 3.40 | 3.40 |
| Sodium Carbonate | — | — | — | 4.00 | 2.50 | — | — |
| TSP 12H$_2$O | 6.10 | 8.80 | 8.49 | — | — | — | — |
| Cabosil EH 5 | 0.94 | 0.97 | 0.89 | 0.92 | 0.96 | 0.94 | 0.94 |
| Total | 100.00 | 100.00 | 100.00 | 100.00 | 100.00 | 100.00 | 100.00 |

| Raw Material | #17 | Pigment Blend | | #19 | #20 | #21 |
|---|---|---|---|---|---|---|
| PVAP-J | 73.00 | Raw Material | #18 | — | — | — |
| Talc 400 | 9.46 | Lake Blend 1368 | 55.00 | 9.46 | 9.46 | 9.46 |
| Stearic Acid | 1.80 | TiO$_2$ | 20.00 | 1.80 | 1.80 | 1.80 |
| Sodium Alginate | 1.40 | PEG 3350 | 10.00 | 1.40 | 1.40 | 1.40 |
| PEG 3350 | 8.00 | Citroflex-2 | 10.00 | 8.00 | 8.00 | 8.00 |
| Citroflex-2 | 2.00 | Tween 80 | 3.00 | 2.00 | 2.00 | 2.00 |
| Sodium bicarbonate | 3.40 | | | 3.40 | 3.40 | 3.40 |
| Cabosil EH 5 | 0.94 | | | 0.94 | 0.94 | 0.94 |
| HPMCP | — | | | 73.00 | — | — |
| HPMCAS | — | | | — | 73.00 | — |
| CAP | — | | | — | — | 73.00 |
| Total | 100.00 | | 100.00 | 100.00 | 100.00 | 100.00 |

| Raw Material | #18 A | #18 B |
|---|---|---|
| #17 Sureteric clear | 94.00 | 87.50 |
| #18 Pigment Blend | 6.00 | 12.50 |

*Citroflex-2 (Triacetin) will be added to the dispersion externally

| Components | EX. 36 | EX. 37 | EX. 38 | EX. 39 | EX. 40 | EX. 41 | EX. 42 | EX. 43 | EX. 44 |
|---|---|---|---|---|---|---|---|---|---|
| | 15% solid | 15% solid | 15% solid | 15% solid | 15% solid | 15% solid | 15% solid | 15% solid | 20% solid |
| % PVAP-T* | 73 | 73.2 | 73.2 | 67.1 | 73 | 70.5 | 73 | 73 | 73 |
| % TALC | 9.46 | 9.46 | 9.46 | 8.67 | 9.46 | 9.1 | 9.4 | 9.46 | 9.46 |
| % Steric acid | 1.8 | 1.8 | 1.8 | 1.65 | 1.8 | 1.74 | 1.6 | 1.6 | 1.6 |
| % So. Alginate | 1.4 | 1.4 | 1.4 | 1.3 | 1.4 | 1.35 | 1.4 | 1.4 | 1.4 |
| % Cabosil | 0.94 | 0.94 | 0.94 | 0.85 | 0.94 | 0.9 | 0.94 | 0.94 | 0.94 |
| % So. Bicarb. | 4 | 3.6 | 3.6 | 3.3 | 3.6 | 3.25 | 3.38 | 3.4 | 3.4 |

-continued

| Components | | | | | | | | | |
|---|---|---|---|---|---|---|---|---|---|
| % Citroflex | 2.3 | 2.4 | 2.4 | 2.2 | 2.1 | 2.2 | 2 | 2 | |
| % Mg Oxide | | | | | 0.4 | 0.36 | 0.36 | 0.2 | 0.2 |
| % PEG 3350 | 7.1 | 7.2 | 7.2 | 15.12 | 7.2 | 10.7 | 7.5 | 7.6 | 7.8 |
| % FG-10 | 1 | 1 | 1 | 1 | 1 | 1 | 1 | 1 | 1 |

| Components | EX. 45 | EX. 46 | EX. 47 | EX. 48 | EX. 49 | EX. 50 | EX. 51 | EX. 52 | EX. 53 | EX. 54 | EX. 55 |
|---|---|---|---|---|---|---|---|---|---|---|---|
| % PVAP-J | | | | 58.03 | | | | | | | |
| % PVAP-T | 74.79 | 71.15 | 68.58 | | 69 | 88.1 | 89.02 | 88.3 | 89.73 | 88.3 | 9.13 |
| % TALC | 9.59 | 9.13 | | | | | 8.88 | 5.75 | 8.95 | 8.78 | 9.13 |
| % Al. Hydrate | | | 10.1 | 9.06 | 8.65 | 10.3 | | | | | |
| % Stearic acid | 1.92 | 1.82 | 2.64 | | 1.9 | 2.8 | 1.77 | 1.75 | 1.78 | 1.75 | 1.82 |
| % So. Alginate | 1.44 | 1.37 | 1.38 | 1.38 | 1.4 | 1.4 | 1.33 | 1.32 | 1.34 | 1.32 | 1.37 |
| % Cabosil | 0.98 | 0.92 | 0.92 | 0.91 | 0.97 | 0.94 | 0.89 | 0.88 | 0.9 | 0.88 | 0.92 |
| % So. Phos. | 4 (anh) | 8.75 | 8.12 | 9.3 | 8.8 | 6.1 | 8.49 | 8.4 | 8.58 | 8.4 | 6.75 |
| % Citroflex | | | | | | | | | 4 | | |
| % PVP | | | | | | | | | 2 | 2 | |
| % PEG 3350 | 7.3 | 6.66 | 10.1 | 11.34 | 9.28 | 10.38 | 6.65 | 6.59 | 6.72 | 8.59 | 8.86 |
| % Pluronic F58 | | | | | | | 3 | | | | |
| % FG-10 | 1 | 1 | 1 | 1 | 1 | 1 | 1 | 1 | 1 | 1 | 1 |

| Components | EX. 56 | EX. 57 | EX. 58 | EX. 59 | EX. 60 | EX. 61 | Ex.62 |
|---|---|---|---|---|---|---|---|
| % PVAP-J | | | | | | | |
| % PVAP-T | 88.03 | 72.6 | 73.55 | 74 | 73.6 | 73 | 73.2 |
| % TALC | | 8.54 | 7.54 | 9.1 | 9.14 | 9.48 | 9.45 |
| % Al. Hydrate | 9.06 | | | | | | |
| % Stearic acid | | 1.76 | 1.72 | 1.75 | 1.72 | 1.8 | 1.8 |
| % So. Alginate | 1.38 | 1.4 | 1.43 | 1.42 | 1.42 | 1.4 | 1.4 |
| % Cabosil | 0.91 | 0.9 | 0.88 | 0.92 | 0.92 | 0.94 | 0.94 |
| % So. Phos. | 9.3 | 5 | 4.53 | | | | |
| % Citroflex | | | | | | 2.3 | 2.4 |
| % Sod. Bicarb | | | | | | 4 | 3.8 |
| % PEG 3350 | 9.34 | 8.8 | 9.07 | 9.3 | 9.3 | 7.1 | 7.2 |
| % Sod. Carb. | | | | 2.54 | 4 | | |
| % Pluronic F88 | 2 | | | | | | |
| % Mg. Oxide | | 1.2 | 1.2 | 0.97 | | | |
| % FG-10 | 1 | 1 | 1 | 1 | 1 | 1 | 1 |

| Components | EX. 63 | EX. 64 | EX. 65 | EX. 66 |
|---|---|---|---|---|
| % PVAP-J | | | | |
| % PVAP-T | 80.84 | 80.64 | 79.1 | 78.41 |
| % TALC | 10.33 | 10.33 | 10.15 | 9.78 |
| % Al. Hydrate | | | | |
| % Stearic acid | 2.06 | 2.06 | 2.02 | 1.95 |
| % So. Alginate | 1.54 | 1.54 | 1.52 | 1.47 |
| % Cabosil | 1.04 | 1.04 | 1.01 | 0.98 |
| % So. Phos. | 4.38 (anh) | 4.38 (anh) | 6.2 | 9.4 |
| % Citroflex | 10.8 | 10.9 | 10.7 | 10.32 |
| % PEG 3350 | | | | |
| % Pluronic F88 | | | | |
| % FG-10 | 1 | 1 | 1 | 1 |

| Components | EX.67 | EX. 68 | EX. 69 | EX. 70 | EX. 71 | EX. 72 | EX. 73 | Ex. 74 | EX. 75 | EX. 76 | EX. 77 | EX. 78 | EX. 79 |
|---|---|---|---|---|---|---|---|---|---|---|---|---|---|
| % PVAP-J | 75.6 | | | 75.42 | | | 79.69 | | | | | | |
| % PVAP-T | | 76.24 | 78.23 | | 80 | 80.11 | | 60.8 | 80.73 | 80.84 | 72.8 | 73.45 | 80 |
| % TALC | 9.7 | 9.77 | 9.77 | 9.67 | 8 | 10.27 | 10.22 | 10.27 | 10.32 | 10.33 | 9.31 | 9.41 | 8 |
| % Al. Hydrate | | | | | | | | | | | | | |
| % Stearic acid | 1.94 | 1.95 | 1.95 | 1.93 | | 2.05 | 2.04 | 2.05 | 2.06 | 2.07 | 2.06 | 1.68 | 1.88 |
| % So. Alginate | 1.48 | 1.47 | 1.46 | 1.45 | 1.92 | 1.54 | 1.83 | 1.5 | 1.55 | 1.54 | 1.4 | 1.48 | 1.92 |
| % Cabosil | 0.97 | 0.97 | 0.98 | 0.97 | | 1.03 | 1.02 | 1.03 | 1.04 | 1.04 | 0.93 | 0.95 | |
| % So. Phos. | 10.33 | 9.8 | 9.61 | 10.58 | 10.05 | 5 (anh) | 5.5 (anh) | 4.5 (anh) | 4.29 (anh) | 4.39 (anh) | 3.67 (anh) | 3.9 (anh) | 10.08 |
| % Citroflex | | | 10.29 | 11.09 | | | | | | | | | 10.08 |
| % Triacetin | 10.38 | 10.29 | | | 10.5 | 10.61 | 11.95 | 10.87 | 10.9 | 10.9 | 9.53 | 5.93 | |
| % Pluronic F88 | | | | | | | | | | | | | |
| % FG-10 | 1 | 1 | 1 | 1 | 1 | 1 | 1 | 1 | 1 | 1 | 1 | 1 | 1 |

| Components | EX. 80 | EX. 81 | EX. 82 | EX. 83 | EX. 84 | EX. 85 | EX. 86 | EX. 87 | EX. 88 | EX. 89 | EX. 90 | EX. 91 | EX. 92 | EX. 93 |
|---|---|---|---|---|---|---|---|---|---|---|---|---|---|---|
| % PVAP-T | 70.92 | 72.5 | 70.13 | 70.92 | 67.77 | 73.29 | 70.92 | 69.35 | 58.58 | 72.5 | 70.13 | 89.35 | 66.98 | 69.35 |
| % TALC | 10 | 5 | 6 | 7 | 10 | 8 | 10 | 8 | 10 | 8 | 5 | 9 | 10 | 9 |
| % Stearic acid | 0 | 2 | 1 | 0.5 | 0 | 0 | 0 | 2 | 2 | 2 | 1 | 1.5 | 2 | 0.5 |
| % So. Alginate | 1.42 | 1.45 | 1.4 | 1.42 | 1.38 | 1.47 | 1.42 | 1.39 | 1.37 | 1.45 | 1.4 | 1.39 | 1.34 | 1.39 |
| % Cabosil | 0 | 0 | 0.5 | 0.25 | 1 | 1 | 0 | 1 | 1 | 0 | 0.5 | 0.75 | 0 | 0.25 |
| % So. Phos. | 8.72 | 5.92 | 8.63 | 8.72 | 8.34 | 9.01 | 6.72 | 6.53 | 8.43 | 8.92 | 8.63 | 8.53 | 8.24 | 8.53 |

-continued

| | | | | | | | | | | | | | |
|---|---|---|---|---|---|---|---|---|---|---|---|---|---|
| % PEG 3350 | 8.94 | 9.13 | 8.84 | 8.94 | 8.64 | 9.23 | 6.94 | 8.74 | 8.54 | 9.13 | 6.64 | 6.74 | 6.44 | 8.74 |
| % Pluronic F88 | 0 | 0 | 1.5 | 2.26 | 3 | 0 | 0 | 3 | 0 | 0 | 1.5 | 0.75 | 3 | 2.25 |
| % FG-10 | 1 | 1 | 1 | 1 | 1 | 1 | 1 | 1 | 1 | 1 | 1 | 1 | 1 | 1 |

The percent solids in the enteric coating suspensions of the invention are about 10% to about 30%, and preferably is about 12% to about 20%.

It is preferred, but not necessary, to provide a subcoat and a topcoat, such as those described in Examples 1 and 2, on a tablet coated in accordance with the invention. Preferably, the subcoat and the topcoat each comprise, typically, 1–10% of the weight of the tablet, depending on the size, weight, and shape of the tablet. Typically, a small tablet requires a larger percentage of subcoat and topcoat by weight of the tablet then does a larger tablet.

The enteric coating of the invention comprises, typically, greater than 6% of the weight of the tablet, and preferably between 8% to 12% by weight of the tablet in order to get the enteric results, depending on the size, weight, and shape of the tablet. A small tablet requires a larger percentage of coating by weight of the tablet for enteric coating then does a larger tablet.

Tablets coated with the inventive coating suspension have an intestinally soluble coating that is insoluble in the gastric juices of the stomach.

Without the step of adding an antifoaming agent in the method of making the enteric coating suspension of the invention, air bubbles tend to be incorporated into the suspension during mixing of the dry ingredients into the water. Air bubbles, if present in the coating suspension during spraying onto tablets substrates may create pin holes in the film coating, which may lead to failure of the enteric film coating. Further, some of the alkalizing agents, such as sodium bicarbonate, are effervescent, and mixing them into the water of the enteric coating suspension may lead to the formation of additional air bubbles in the enteric coating suspension. Also, sodium alginate tends to maintain any foam or bubbles formed in the enteric coating suspension. The antifoaming agent fights against the incorporation of air bubbles in the enteric coating suspension by causing air bubbles in the enteric coating suspension to rupture.

The enteric coating of the invention provides an improvement of film properties over the film properties of known enteric film coatings based on aqueous enteric coating suspension. For example, the coating of the invention, when compared with known coatings based on aqueous enteric coating suspensions, has better adhesion, is more resilient, is less friable, and has a significantly lower modulous of elasticity. Further, using a preferred embodiment of the inventive enteric dry powder composition which contains a plasticizer, our inventive aqueous enteric coating suspension requires only two processing steps to form the enteric coating suspension of the invention—mixing antifoam with water and then mixing the enteric powder composition into the antifoam/water mixture.

A comparison of the inventive SURETERIC system with other enteric aqueous systems appears below.

| | SURETERIC | EUDRAGIT | AQUATERIC | COATERIC |
|---|---|---|---|---|
| PREPARATION | Mix powder & antifoam | Mix plasticizer, | Mix powder, plast- | Mix powder, |

-continued

| | SURETERIC | EUDRAGIT | AQUATERIC | COATERIC |
|---|---|---|---|---|
| STEPS | with water | antifoam, & talc with dispersion | icizer & Tween 80 with water | antifoam, & ammonia with water |
| PREPARATION STEPS | 2 | 3 | 3 | 3 |
| PREPARATION TIME | 45–60 min. | 60 min. | 90–110 min. | 60 min. |
| PROCESS PROBLEMS | 1. Slight Tack | 1. Tack, 2. High % of talc settles rapidly, 3. Prone to gun clogs | 1. 60 min. post-drying step | 1. Tack, 2. Ammonia unpleasant to work with |

We claim:

1. A method of coating substrates such as pharmaceutical tablets with an enteric film coating, comprising
    mixing an antifoaming agent into water,
    mixing an enteric film forming polymer, a detackifier, a viscosity modifier, an alkalizing agent, and a plasticizer into the water to form an aqueous enteric coating suspension,
    applying the aqueous enteric coating suspension onto the substrates to form an enteric film coating on the substrates, and
    drying the enteric film coating on said substrates.

2. The method of claim 1, further including the step of mixing a lubricant into the water.

3. The method of claim 1, further including the step of mixing an anti-caking agent into the water.

4. The method of claim 1, further including the step of mixing a pigment into the water.

5. The method of claim 1, further including the step of mixing a lubricant, an anti-caking agent, and a pigment into the water,
    the enteric film forming polymer being PVAP-T (titanized polyvinyl acetate phthalate), PVAP-J (polyvinyl acetate phthalate which has been jet milled), HPMCP (hydroxypropyl methylcellulose phthalate), HPMCAS (hydroxypropyl methylcellulose acetate succinate), or CAP (cellulose acetate phthalate),
    the polymer being in a range of about 65% to about 81% by weight of the non-water ingredients of the suspension,
    the detackifier being talc, aluminum hydrate, or mixtures thereof,
    the detackifier being in a range of about 6% to about 12% by weight of the non-water ingredients of the suspension,
    the viscosity modifier being sodium alginate, HPMC (hydroxypropyl methylcellulose), HEC (hydroxyethylcellulose), sodium CMC (sodium carboxymethylcellulose), PVP (polyvinyl pyrrolidone), Konjac flour, carrageenan, xanthan gum, other hydrophilic polymers, or mixtures thereof, the viscosity modifier being in a range of about 1% to about 6% by weight of the non-water ingredients of the suspension, the alkalizing agent being a bicarbonate, a carbonate, a phosphate, or a hydroxide of sodium or potassium, magnesium carbonate, magnesium hydroxide, ammonium carbonate, ammonium bicarbonate, magnesium oxide, calcium hydroxide, or mixtures thereof, the alkalizing agent being in the range of about 1.5% to about 12% by weight of the non-water ingredients of the suspension, the plasticizer being in a range of about 5% to about 20% by weight of the non-water ingredients of the suspension, the plasticizer being a solid plasticizer, a liquid plasticizer, or a combination thereof, the solid plasticizer being polyethylene glycol 1500, polyethylene glycol 3350, polyethylene glycol 4000, polyethylene glycol 8000, or Pluronic F86, the liquid plasticizer being triethylcitrate, glyceryl triacetate, acetyltriethylcitrate, dibutyl sebacate, diethyl phthalate, polyethylene glycol 400, glycerol, castor oil, or mixtures thereof, the lubricant being stearic acid, the lubricant being in a range greater than 0% to about 3% by weight of the non-water ingredients of the suspension, the anti-caking agent being silica, the anti-caking agent being in a range of greater than 0% to about 1.5% by weight of the non-water ingredients of the suspension, the pigment being lake blends with plasticizer, FD&C and D&C lakes, titanium dioxide, or OPADRY non-clear film coating compositions, the pigment being in a range from greater than 0% to about 15% by weight of the non-water ingredients of the suspension, the antifoaming agent being a silicone based antifoam, and the antifoaming agent being in a range of about 0.5% to about 5% by weight of the non-water ingredients of the suspension.

* * * * *